(12) United States Patent
Beutler et al.

(10) Patent No.: US 9,592,261 B2
(45) Date of Patent: Mar. 14, 2017

(54) COMPARTMENT-SPECIFIC PLANT EXTRACT COMBINATION OF GINKGO BILOBA EXTRACT AND GINSENG EXTRACT HAVING A TANDEM EFFECT

(75) Inventors: Rolf D. Beutler, Hoechst/Hummetroth (DE); Karlheinz Schmidt, Gomaringen (DE)

(73) Assignee: Dr. Willmar Schwabe GmbH & Co. KG, Karlsruhe (DE)

( * ) Notice: Subject to any disclaimer, the term of this patent is extended or adjusted under 35 U.S.C. 154(b) by 1793 days.

(21) Appl. No.: 12/736,440

(22) PCT Filed: Sep. 9, 2008

(86) PCT No.: PCT/EP2008/007357
§ 371 (c)(1),
(2), (4) Date: Oct. 8, 2010

(87) PCT Pub. No.: WO2009/129833
PCT Pub. Date: Oct. 29, 2009

(65) Prior Publication Data
US 2011/0034563 A1 Feb. 10, 2011

(30) Foreign Application Priority Data
Apr. 22, 2008 (DE) .................. 10 2008 020 127

(51) Int. Cl.
| A61K 36/16 | (2006.01) |
| A61K 36/25 | (2006.01) |
| A61K 36/734 | (2006.01) |
| A61K 36/258 | (2006.01) |
| A61K 36/254 | (2006.01) |

(52) U.S. Cl.
CPC ............ *A61K 36/258* (2013.01); *A61K 36/16* (2013.01); *A61K 36/254* (2013.01); *A61K 36/734* (2013.01)

(58) Field of Classification Search
CPC ......... A61K 36/16; A61K 36/25; A61K 36/73
USPC ........................................ 424/728, 752, 765
See application file for complete search history.

(56) References Cited

U.S. PATENT DOCUMENTS

| 6,617,356 B2 * | 9/2003 | Goodman ............... A61K 36/16 424/752 |
| 2009/0238902 A1 | 9/2009 | Liu |

FOREIGN PATENT DOCUMENTS

| CN | 1341432 A * | 3/2002 | |
| CN | WO 2007124674 A1 * | 11/2007 | ............ A61K 36/16 |
| DE | 600 09 145 | 7/2004 | |
| DE | 10 2006 019 863 | 11/2006 | |
| EP | 1 242 105 | 9/2002 | |
| EP | 1 537 874 | 6/2005 | |
| GB | WO 0143753 A2 * | 6/2001 | ............ A61K 36/16 |
| JP | 2003-038140 | 2/2003 | |
| WO | WO 01/43753 | 6/2001 | |
| WO | WO 2007/045959 | 4/2007 | |
| WO | WO 2007/118363 | 10/2007 | |
| WO | WO 2007/124674 | 11/2007 | |

OTHER PUBLICATIONS

International Search Report.
German Office Action dated Dec. 10, 2008 with English translation of relevant parts.
Martindale: The Complete Drug Reference; Pharmaceutical Press 2007: Contents: Energeia[1], Extralife Extra-Brite[3], Fosfaserin[3], Gincosan[1], Gingo-Ther[1], Ginkovit[1], Ginkgo Biloba Plus[2], Ginkgo Complex[2], Top Life Memory[1], Triallin[2]; ISBN: 0 85369 553; 978 0 85369 703 9 (CD-ROM). (German OA).
HagerROM 2006, Hagers Handbuch der Drogen and Arzneistoffe (Hager's Handbook of Drugs and Medicine), Springer-Verlag; keyword: Ginseng radix, Ginkgo-biloba-leaves; ISBN: 3-540-28232-7. (With English translation of relevant parts) (German OA).
Wesnes, K. A. et al., "The memory enhancing effects of a Gingko biloba/Panax ginseng combination in healthy middle-aged volunteers," Psychopharmacology, Springer Verlag, Berlin, Germany, vol. 152, No. 4, Jan. 1, 2000, pp. 353-361, XP001029198, (ISR).
Iwaoka Emiko et al., "Preventive effect of the Chinese herbal medicine 'Myakuryu' on hypertension and stroke in stroke-prone spontaneously hypertensive rats," Clinical and Experimental Pharmacology and Physiology, vol. 34, No. Suppl. 1, Nov. 2007, pp. S51-S52, XP002542482. (ISR).

* cited by examiner

*Primary Examiner* — Chris R Tate
*Assistant Examiner* — Deborah Davis
(74) *Attorney, Agent, or Firm* — Collard & Roe, P.C.

(57) ABSTRACT

The invention relates to a plant extract combination of *ginkgo* and *ginseng* which is effective especially in a (synergistic) over-additive manner and optionally comprises whitethorn extract. *Ginseng* is used in the form of an ethanol/ethanol/water extract while *ginkgo* is used in the form of an acetone/acetone-water extract, for example, and the active extracts are prepared at specific quantitative ratios, particularly <1.1:1, thus unexpectedly boosting the prevention or also the treatment of a decline in the mental capacity related to age or also other disorders. This results from an over-additive tandem effect by protecting neural cells and improving blood circulation while increasing energy supply and activating cerebral metabolism, not only in the cognitive-therapeutic field, an effect being obtained against harmful oxidative influences caused especially by decomposition products of effective substances, whereby in particular antioxidative protection extends in a complementary manner to several cell compartments.

9 Claims, 1 Drawing Sheet

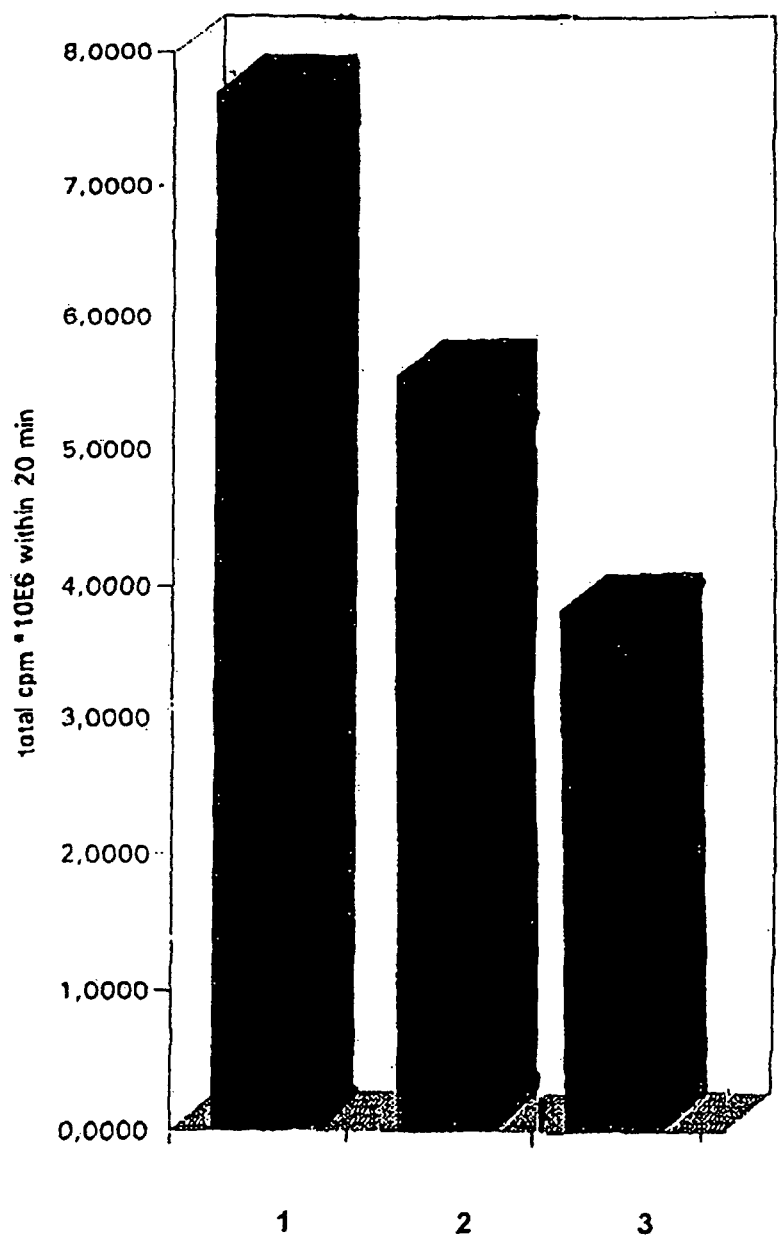
(1 = control, 2 = ginkgo extract, 3 = ginkgo + ginseng extract)

COMPARTMENT-SPECIFIC PLANT EXTRACT COMBINATION OF GINKGO BILOBA EXTRACT AND GINSENG EXTRACT HAVING A TANDEM EFFECT

CROSS REFERENCE TO RELATED APPLICATIONS

This application is the National Stage of PCT/EP2008/007357 filed on Sep. 9, 2008, which claims priority under 35 U.S.C. §119 of German Application No. 10 2008 020 127.8 filed on Apr. 22, 2008, the disclosure of which is incorporated by reference. The international application under PCT article 21(2) was not published in English.

OBJECT OF THE INVENTION

The present invention relates to a plant extract combination of ginkgo and ginseng, which has a particularly (synergistically) super-additive effect, with the optional addition of hawthorn powder or hawthorn extract, whereby ginseng extract and ginkgo extract are used in a ratio of particularly ≤1.1:1. In this way, improved prevention, if applicable also treatment, can be achieved, in unexpected manner, with regard to a reduction in mental performance such as attention, concentration, memory, caused by aging or also by other problems. This results from a super-additive tandem effect by means of protection of neuronal cells and improved blood circulation, on the one hand, together with an improved energy supply and activation of the brain metabolism, on the other hand, not just in the cognitive-therapeutic sector. In particular, harmful influences caused by oxidation, primarily due to decomposition products of active substances, can be counteracted with the combination according to the invention, and in this way, anti-oxidative protection, in particular, can be extended in complementary manner to cover multiple cell compartments.

STATE OF THE ART

Plant extracts in the form of nutritional supplements or plant-based medications (phytopharmaceuticals) have been used for a long time to improve well-being or for treatment of the most varied disorders, on the one hand due to known effects and on the other hand also because their side effects are generally low and they are well tolerated. Depending on the area of use, suitable plants are selected, in each instance, and appropriate forms of administration are produced from them. The effective ingredients can be obtained in different ways. A proven method is extraction by means of solvents. In this connection, a liquid extract, a gel extract, or also a dry extract can be obtained, depending on the plant and/or the desired subsequent form of administration. Since the active substance content of the medicinal plant itself can vary, depending on the location, the weather conditions, and the time of harvesting, the methods for its recovery are coordinated, in each instance, and the extraction method from the collection of the plant to the finished preparation, ready for use, is monitored, in order to guarantee uniform quality of the products.

In recent years, a great number of known plant extracts have established themselves as phytopharmacological products, such as arnica, horse chestnut extract, chamomile, aloe vera, green tea, Echinacea, for use in inflammations, arterial or venous complaints, skin function problems, for strengthening the immune system, etc., whereby both topical and enteral administration can be possible.

Another plant that has been known for a long time is *Panax ginseng* (Korean *ginseng* according to C. F. Meyer). This is used as an ingredient in tonics and generally has a stimulating or vitalizing effect on brain function, such as, for example, an increase in performance ability, in cases of concentration weakness, or strengthening and invigoration also during convalescence. Hawthorn (*Crataegus*) is also a known medicinal plant, which has traditionally been suggested to support cardiovascular function and to increase the ability to withstand stress. Particular attention has been paid to *ginkgo biloba*, which has recently been used frequently by itself or in combination with other active ingredients such as horse chestnut. In this connection, it is generally thought that *ginkgo biloba* can be used as a remedy for improving circulation and oxygen supply, and therefore can be effectively used primarily for treatment of problems related to the brain as an organ, concentration fluctuations, memory weakness, mood instability. For this purpose, a standardized *ginkgo* extract from leaves of the *ginkgo* tree, having a proportion of *ginkgo* flavonglycosides, which are considered to be the effective substance group, of generally 24-36% is used. Such an extract is, for example, *ginkgo* extract Egb761®, which is particularly supposed to be effective after damage to nerve cells, in other words therapeutically. This is an acetone extract (Tebonin®, Egb761®) having a drug/extract ratio of 35-67:1 and 22-27% *ginkgo* flavon-(ol)-glycosides. In the product Ginkobil-N-Ratiopharm®, a *ginkgo* extract is used that contains 40 mg dry extract from *ginkgo biloba* leaves with a standardized amount of 8.8 to 10.8 mg flavonglycosides per 40 mg coated tablet. The remedy is supposed to be used, for example, to treat dementia syndrome and arterial occlusion disease. For this purpose, 1-2 tablets 3× a day, in other words 120 to 240 mg *ginkgo* extract, are recommended.

In DE 600 09 145 T2 (EP 1 242 105 B1), a *ginkgo* extract together with *Panax ginseng* (root) extract is proposed for increasing the cognitive capacity of healthy children and young adults, directly ahead of a known need situation, such as examinations or other mental challenges. For this purpose, a combination is used in which the weight proportion of *ginseng* extract is 1.6 times greater than the weight proportion of *ginkgo* extract. It is reportedly possible to obtain the latter with water/ethanol, or mixtures thereof, or oils. Also, Gincosan® is reportedly suitable, which contains 60 mg *ginkgo* extract GK501 with 24.5% *ginkgo* flavonoids, and 100 mg *Panax ginseng* C. H. Meyer extract G115 (drug/extract ratio 5:1) with 4% ginsenosides, ratio of *ginseng*:*ginkgo* 1.66:1. It is assumed that this combination might exert a blood-platelet-aggregation-inhibiting effect, or also an immunomodulating effect. Good test results have reportedly been achieved here, with at least more than 200 to 1200 mg combination preparation, preferably 320, 640, 960 mg combination preparation, the latter corresponding to the lower monograph dosage (120 mg *ginkgo* and from approximately 1 g *ginseng*, respectively), from 100% *ginkgo* or from approximately 100% *ginseng*, respectively, or up to 150% of the maximal monograph dosage (240 mg *ginkgo*, 2000 mg *ginseng*), for example orally 0.5 to 6 hours before the challenge.

Thus, special extracts and/or special combinations are made available for very specific treatments.

Task of the Present Invention

There continues to be a need for remedies with which reductions in mental performance that are age-related or caused by other disturbances can be reliably prevented and therefore also effectively countered. It would be desirable, in this connection, if the overall complex of brain performance/circulation/oxygen utilization could be addressed, and as a result, the arterial performance of the cardiovascular system could also be positively addressed, by way of maintaining or improving the performance of the brain as an organ.

Solution for the Task

This task is accomplished, according to the invention, in that a combination of *ginkgo biloba* extract and *ginseng* extract is made available, with which it is possible to achieve *ginkgo*-related neuronal cell protection by means of preventive and also therapeutic use, and therefore improved brain circulation, together with an improved supply of energy to the cells and thus an improvement in brain metabolism, brought about by *ginseng* and as a result of the combination, in super-additive manner. This leads to effective prevention of a reduction in mental performance capacity, particularly due to aging, and can be seen in improved attention, concentration, memory performance. The combination according to the invention, in contrast to the remedies described above, above all has an acetone, particularly an acetone/water *ginkgo biloba* leaf extract (dry), for example drug/solvent ratio 35-67:1, preferably 40-53:1, above all 45-49:1, and particularly 50:1, and a *ginseng* extract, above all *Panax ginseng* extract, for example an ethanol or ethanol/water extract, having a drug/extract ratio of 4-3:1, for example, preferably 3.3-3.8:1, above all 3.6:1, whereby the (weight) ratio of *ginseng* extract to *ginkgo* extract is particularly 1.1:1, above all ≤1:1 to 0.7:1, for example. Surprisingly, a super-additive compartment-specific antioxidant effect, in particular, can be achieved by means of the tandem effect according to the invention, in that oxidative, harmful influences brought about by the decomposition products of the active substances, in each instance, are counteracted, and in this way antioxidant protection is extended in complementary manner to multiple cell compartments, leading to an unexpected improvement in the energy availability and utilization of the cell metabolism. This surprisingly leads to an improved tolerance of the cells with regard to oxygen deficiency states (hypoxias), and also to accelerated adaptation of the nutrient demand situation, not only during treatment but already prophylactically.

Preferably, in contrast to previous combinations, the (weight) ratio of *ginkgo* extract to *ginseng*—preferably *Panax ginseng*—extract amounts to 1.4:1 to 0.8:1, above all 0.9:1, particularly 1.4:1 to 1.25:1, above all 1.3:1 to 1.2:1, advantageously also up to 1.1:1 or also 1.1:1, in another embodiment also 1:1. Advantageously, the *ginkgo* extract has 15-30%, or also 17-28%, particularly 18-27% *ginkgo* flavonglycosides, and the *ginseng* extract has 3-6%, particularly 3.5-5%, or also 4% ginsenosides.

Such a combination, having a synergistic antioxidant complementary tandem effect, in which the proportion of *ginseng*, particularly *Panax ginseng*, extract is not significantly greater and particularly equal to or above all less than the amount proportion of *ginkgo biloba* extract, can also have a proportion of hawthorn (*Crataegus*), in another preferred embodiment, as described in the following.

As has been explained, a different effect, in each instance, takes place for the plant extracts, in each instance, which leads to synergy effects when combined, and thus contains a preventive effect. The neuronal protection effect brought about by *ginkgo*, in the sense of an improved tolerance against hypoxic states, can be increased, in this connection, by *ginseng* at the amount ratio indicated, and this in turn leads to an improvement in the energy availability brought about by *ginseng*.

In this connection, a correlation with superoxide dismutase (SOD) can also be assumed for *ginseng*, in surprising manner, whereby in total, an adaptogenic effect (accelerated adaptation of the body functions to corresponding performance demands) stands in the foreground. The addition of *Crataegus* unexpectedly leads to a further protective effect in the cardiological sector. In this way, the particularly prophylactic effect of the combination according to the invention can be further reinforced. In this connection, it can be assumed—without being bound by a specific theory—that because of the tandem effect, an effect extends to cover multiple compartments of the cells, whereby potentially harmful intermediate products in the reaction of the one component are effectively detoxified by means of the reaction with the other component(s).

More Detailed Explanation of the Invention and Preferred Exemplary Embodiments

Combinations produced according to the invention comprise *ginkgo biloba* (from leaves) and *ginseng*, above all *Panax ginseng* (above all *ginseng* root), in the form of—preferably dry—extracts, in each instance, whereby the (weight) ratio of *ginkgo* extract to *ginseng* extract amounts to 1.4:1, above all 1.3:1 to 0.9:1, particularly 1.15:1 or 1:1. Preferably, the drug/extract ratio in the case of *ginkgo biloba* lies between 35-67:1, 47-53:1, preferably 50:1. The *ginkgo* extract (above all acetone/water 60:40) above all has 15-30, above all 18-27% *ginkgo* flavonglycosides, and the *ginseng* (particularly root) extract, which is preferably an alcohol extract, particularly ethanol or ethanol/water extract, for example 20:80 to 60:40 (m/m), preferably *Panax ginseng* 60% ethanol/water extract, has 2-6%, above all 2.4 to 5%, and particularly 3.5-4% ginsenosides.

Combinations in which the (weight) ratio of *ginkgo* to *ginseng* extract amounts to 1.4:1 to 1:0.75, above all 1.4:1 to 1.25:1, and very particularly preferably 1.4:1, are particularly preferred.

Other advantageous embodiments comprise combinations in which 19-30%, preferably 18-27% *ginkgo* flavonglycosides are present in the *ginkgo* extract.

In another advantageous embodiment of the present invention, the combination additionally has a proportion of *Crataegus* spec. (dry powder), for example from a) hawthorn fruits (berries) and/or b) hawthorn leaves/flowers or mixtures thereof, for example in a ratio of 3:1 to 1:3, preferably 1.6:1 to 1:2, particularly 1.5:1 to 1:1 (with reference to leaves/flowers in relation to fruits). The amount of *Crataegus* spec. can amount to 5-40 wt.-%, preferably 10 to 35 wt.-%, particularly 12 to 22 wt.-%, with reference to the total weight of the combination, and the weight ratio of *ginkgo biloba* to *Crataegus* spec. (total) extract can amount to 1:1 to 1:1.3, preferably 1:1.

Production of the Extracts

As has been explained, according to the invention, a non-ethanol/oily solvent extract of *ginkgo biloba* leaves is used. The leaves, which are obtained from specially controlled planting, can be used as such or in dried form. Preferably, they are dried, then purified mechanically in usual manner (by means of screening), ground to the desired grain size in generic drug mills, and subsequently extracted in solvents, for example acetone or above all an acetone/water mixture, for example 40:60 to 70:30 (m/m), particularly acetone:water 60:40 (m/m). The extract obtained, which is generally thin, can, if necessary after other processing steps, be subjected to gentle thickening, for example, or subsequent gentle drying (for example in a vacuum). In this connection, a thick extract or powder is obtained, which can be ground to a desired grain size, if necessary. The ratio of dry drug to native extract then preferably corresponds to 42-56:1, particularly 50:1.

*Ginseng* root dry extract, obtained by means of solvent extraction and processing as described above, is used as a further combination component. Here, preferably alcohol or an alcohol/water mixture, such as ethanol/water 40:60 to 60:40, preferably 60:40 ethanol/water (v/v) is used as an extractant. Here again, a dry extract (powder) is made available as described above. Preferably, *Panax ginseng* roots are used and extracted with ethanol/water 60:40 (v/v). As the end result, a *Panax ginseng* drug/extract ratio 3-4:1, for example, particularly 3.6:1, is obtained. Ethanol/water, 60:40 (v/v), is preferred for a *ginseng* root extract, above all, particularly *Panax ginseng* root containing 3-6% ginsenosides.

Alternatively, if necessary, a Siberian *ginseng Eleutherococcus senticosus* root extract, particularly with a drug/extract ratio of 4-3:1, above all 3.3-3.8:1, preferably 3.6:1 *Eleutherococcus senticosus*, for example an ethanol extract—above all an ethanol/water extract, for example 30:70 to 60:40, preferably 30:70 (v/v) ethanol/water can be used. The ratio of *ginkgo* extract to *Eleutherococcus senticosus* extract can preferably amount to 0.85:1 to 1.4:1, particularly 0.9:1 to 1.3:1, particularly 1.4:1 to 1.25:1, or also 1:1, preferably 1:1 or 1.15:1.

If hawthorn is additionally used, fruits (berries), leaves, and flowers can preferably be selected for this purpose. The starting material is dried, if necessary ground to the desired grain size, and obtained as a powder. Essential ingredients are flavonoids, procyanidines. Preferably, the combination according to the invention can have 15-40 wt.-%, particularly 25-35 wt.-%, with reference to the total weight of the combination, of *Crataegus* spec. powder. This can particularly be a mixture of leaves+flowers together with fruits, for example in the ratio of leaves+flowers:fruits (berries) of 1:2 to 2:1. Mixtures of flowers+leaves (for example in a ratio of 1:10 to 10:1) together with berries in a ratio of 1:2 are preferred (powder, as described, in each instance).

Alternatively, a *Crataegus* extract can also be used. The extractant here is preferably alcohol or an alcohol/water mixture, for example 35:65 to 65:35%, preferably 40:60, particularly 45:55% (v/v). Ethanol is particularly suitable as an alcohol. The method is structured as described above. After drying, powder extracts are obtained. These can above all be used in amounts of 5-15 wt.-%, with reference to the total amount of the combination. The powder extracts can preferably contain 1-3, particularly 1-2% flavonoids and 0.4-4% procyanidines.

It is furthermore advantageous if a mixture of hawthorn fruits (berries) (powder), hawthorn leaves with flowers (powder) is present, preferably in the ratio as indicated above.

Description of the Combination Remedies

The combinations according to the invention (*ginkgo* leaves dry extract, *ginseng*—above all *Panax ginseng*—root dry extract, if applicable hawthorn, in the form of dried leaves, fruits, flower powder, if applicable extract powder), can be present as nutritional supplements or particularly as a (pharmaceutical) medication, phytopharmaceutical, above all for prevention and also therapeutically. For this purpose, the active substance combinations can be mixed with suitable additives, such as those that are known for the production of dragees, tablets, coated tablets, capsules, such as, for example, disintegrants, fillers, flow agents, carriers, tablet-production aids, silicon dioxide and its derivatives, cellulose and its derivatives, magnesium stearate, lactose, saccharose, wax, oils such as soybean oil, phospholipids, polyols such as sorbitol, starch powder, cellulose esters or alkanoic acids, cellulose alkyl esters, talcum, stearic acid, magnesium oxide, sodium and calcium salts of phosphoric and sulfuric acids, gelatins, acacia gum, sodium alginate, glycols, polyvinyl pyrrolidone, and/or polyvinyl alcohol, and then, in tablet or capsule form, also combined with dissolution aids such as citric acid, hydrogen carbonate, if necessary. These additives and their required or desired amounts are generally known to a person skilled in the art. Particularly preferred ancillary substances, aside from other oils such as soybean oil, coconut fat, and/or phospholipids, for example from soybeans, are egg, gelatin, glycerol, polyols such as sorbitol, lactose, saccharose, phosphates such as calcium hydrogen phosphate, talcum, pigments, cellulose and its derivatives, silicon dioxide and its derivatives, waxes, starch. Particularly preferred ancillary substances, aside from usual additives, are phospholipids.

Using combinations according to the invention, it is possible to prepare suitable effect units with regard to the monograph daily dosage. These include, for example, dragees or tablets/capsules. These can be obtained, for example, from 10-30%, particularly 14-29% *ginkgo;* 10-28%, particularly 12-24% *ginseng* (*Panax ginseng*), and, if applicable, 1.5-6%, above all 2.5-5.3% *Crataegus* of the recommended monograph daily dosage, in each instance. Such effect units can preferably be administered, so that a daily dose between 80-86%, for example (with reference to the maximal dosage)—100-120, for example 115% (with reference to the lower dosage), above all 86% *ginkgo*, or 25% (upper dosage) to 75% (lower dosage), particularly up to 37% (with reference to the maximal dosage) *Panax ginseng*, as well as, if applicable, 5 to 13%, particularly 5 to 10%, above all 10% *Crataegus* (with regard to *Crataegus*, recommended dosage approximately 1500 mg) is reached. Preferably, effect units (with reference to the lower monograph daily dosage) of approximately 27-29% *ginkgo*, 11-13% *ginseng*, and, if applicable, 2-3% *Crataegus* are prepared. This means that the almost maximal dose or above does not have to be used for all the active ingredients. Although the extracts selected are currently considered safe and non-toxic, it is nevertheless advantageous if less active substance, as a whole, is required.

Use/Method of Effect

On the basis of various studies, the recognition has been solidified that oxidative changes, for example, of both the neuro-geriatric and the cardiovascular symptom complex in important cell structures can lead to at first mostly uncharacteristic general symptoms that can be circumscribed with the term "age-related performance reduction."

Using the combinations according to the invention, a tandem effect can be achieved, in that the effects brought about by the extracts, in each instance, reciprocally reinforce one another: Thus it can be assumed that *ginkgo* extract leads to neuronal protection with better circulation in the brain, while an increased energy availability is achieved by *ginseng*, as a result of its use. Surprisingly, an optimal, more comprehensive, particularly prophylactic effect can be achieved by means of this synergy of protection and energy. This also becomes evident from the following examples, particularly also in the proof test of chemiluminescence. All in all, this is a compartment-specific tandem effect—without being tied to a specific mechanism—in that different protection also against oxidant/harmful influences caused by the decomposition products of the active substances, in each instance, can be achieved, and thereby the antioxidant/neuronal (protection) effect extends in complementary manner to cover multiple cell compartments, and thus the energy availability for this can be improved. As a result, not only a specific neuronal/mitochondrial regeneration effect, but also a general preventive/therapeutic effect can be achieved.

In this regard, combinations according to the invention are suitable for preventive and/or therapeutic use or for the production of remedies for this use or as supplements, in cases of mental performance problems, for example age-related problems. Age-related performance problems in the sense of the present invention mean: decrease in mental performance capacity (performance problems caused by the brain as an organ and/or capillary-related performance problems), concentration deficiencies, memory loss, or also resulting decreases in physical performance capacity, such as fatigue, irritability, depressed mood, anxiety and dizziness, arterial and peripheral circulation problems.

The efficacy of combinations according to the invention can also be determined in vivo in the COMPASS test (Computerized Mental Performance Assessment), on the basis of the improved memory function (working memory, spatial memory), in selected healthy test subjects. By means of the analysis of delta, theta, alpha, and beta waves, the change in brain activity after taking the combinations according to the invention can be measured according to the Quantitative Pharmaco-Electro-Encephelogram Method.

Production of the Combination Remedies

The combinations according to the invention are produced in known manner and used for the production of the remedies described below, such as tablets, capsules (gelatin capsules), dragees, in that first, the extracts/powders are obtained as described above, and mixed and homogenized, preferably as a powder, in suitable manner, using suitable additives, in each instance, for the desired oral form of administration (particularly solid oral forms such as tablets, dragees, capsules), such as carriers, fillers, tablet-production aids, as mentioned. Methods for the production of such remedies/nutritional supplements, phytopharmaceuticals, or also pharmaceutical remedies have been described in teaching manuals, for example, and are generally known. In this manner, pharmaceutical preparations or also supplements (nutritional supplements) can be obtained, as described.

Use

The combinations according to the invention have been designed particularly for systemic use and for the production of remedies suitable for this purpose, as described above. In this connection, oral forms of administration such as gelatin capsules, for example soft gelatin capsules, as well as tablets, dragees, are suitable for this.

For the production of capsules or tablets, ancillary substances usual for this purpose, such as lactose, saccharose, sorbitol, talcum, oils, soy, stearic acid, magnesium stearate, gum arabic, potato starch, gelatin, PVP, glycerin, hydroxypropyl methyl cellulose, maltodextrin, preservatives, as well as usual materials for coatings such as PEG 6000, corn starch, sugar, talcum, pigments, are used, in known manner. If administration takes place per os, the composition described can be mixed, for example, with lactose, saccharose, starch powder, cellulose esters, or alkanoic acids, cellulose alkyl esters, talc, stearic acid, magnesium stearate, magnesium oxide, sodium and calcium salts of phosphoric and sulfuric acids, gelatin, acacia gum, sodium alginate, glycols, polyvinyl pyrrolidone and/or polyvinyl alcohol, and then be formed into a tablet or capsule.

The additives (see also above) and tablet-production methods are generally known and are described, for example, in the current European Pharmacopoeia.

In particular, the (remedies of the) combination can be used preventively and/or also therapeutically, in this regard, in cases of mental performance reductions or problems, for example age-related problems. Age-related performance reductions or problems in the sense of the present invention mean: decrease in mental performance capacity (performance problems caused by the brain as an organ and/or capillary-related performance problems), concentration deficiencies, reduction in memory performance, or also resulting decreases in physical performance capacity, such as fatigue, irritability, depressed mood, anxiety and dizziness, arterial or peripheral circulation problems.

The amount of the remedy administered and the dosage schedule for prevention or treatment of one of the states as described above with the combinations according to the invention can depend on a plurality of factors (for example in the case of a medical indication), including age, weight, gender, and state of the recipient, the administration route, and can therefore vary to a great extent. The required or desired dose can be divided into once or multiple times a day, particularly one to three times.

In the case of administration as a supplement, amounts usual for this purpose are proposed, which can be divided into once or multiple times a day, particularly one to three times or one to two times. These can be present in solid form, for example as a tablet, capsule, dragee. Particularly preferably, amounts are administered with which the monograph daily dose rations described initially are achieved.

EXAMPLES

The invention will be described in greater detail using the following product examples 1-5, and the evidence of effect will be explained in greater detail in Example 6.

A. Product Examples

Example 1

36 mg of a *ginkgo* leaf powder extract, extractant acetone/water 60:40 (m/m), as described above, drug/extract ratio: 38-57:1, containing 18-27% *ginkgo* flavonglycosides, is mixed with 32.4 mg *Panax ginseng* root dry extract, extractant ethanol/water (60:40, v/v), drug/extract ratio: 2.6-3.5:1, containing 3-5% ginsenoids, with silicon dioxide, corn starch, gum arabic, calcium stearate, hydrogenated cottonseed oil, saccharose, pigments (E 104, E 132), cellulose, in suitable amounts, and processed to produce dragees, coating agent: Eudragit E.

Example 2

A soft gelatin capsule was produced from: soy phospholipids, soybean oil, gelatin, glycerin, glycerol, coconut fat, lactose, mannitol, water, 34 mg *ginkgo* extract powder (acetone/water 60:40), as described above, drug/extract ratio 45-67:1, as well as 35.4 mg *Panax ginseng* root dry extract (ethanol/water 60:40, drug/extract ratio 3-4:1).

Example 3

A dragee was produced from lactose, silicon dioxide, highly dispersed calcium/sodium carbonate, talcum, cellulose, gum arabic, soybean oil, titanium dioxide, pigment E 132, coating agent Eudragit E, as well as 32.4 mg *ginkgo* extract (extract acetone/water 60:40 m/m), drug/extract ratio 50:1, as described above, 23.2 mg *Panax ginseng* extract (extract ethanol/water 60:40, v/v), 35 mg hawthorn (1:1 mixture hawthorn fruits (berries)/hawthorn leaves and flowers, dry powder, in each instance).

Example 4

36 mg of a *ginkgo* leaf powder extract, according to Example 1, extractant acetone/water 60:40, (m/m), as described above, drug/extract ratio: 50:1, containing 18-27% *ginkgo* flavonglycosides, are mixed with 32.7 mg *Panax ginseng* root dry extract, according to Example 1, extractant ethanol/water, 60%, drug/extract ratio: 3.8:1, containing 3-5% ginsenoids, 35 mg hawthorn (2:1 mixture hawthorn fruits (berries)/hawthorn leaves and flowers, dry powder, in each instance), with silicon dioxide, corn starch, gum arabic, calcium stearate, hydrogenated cottonseed oil, saccharose, pigments (E 104, E 132), cellulose, in suitable amounts, and processed to produce dragees, coating agent: Eudragit E.

Example 5

36 mg of a *ginkgo biloba* leaf powder extract, extractant acetone/water 60:40 (m/m), as described above, drug/extract ratio: 50:1, containing 18-27% *ginkgo* flavonglycosides, are mixed with 34.4 mg *Eleutherococcus senticosus* root dry extract, extractant ethanol/water, 30:70 (v/v), drug/extract ratio: 3.8:1, containing 3-5% ginsenoids, with highly dispersed silicon dioxide, hypromellose, lactose monohydrate, Macrogol 400, magnesium stearate, talcum, iron (III) oxide E 172, titanium dioxide E 171, soybean oil, gelatin, yellow wax, sorbitol, in suitable amounts, and processed to produce dragees, coating agent: Eudragit E.

B. Evidence of Effect

Example 6

The antioxidant effect that stands in a relationship with decreasing memory function was determined using the chemiluminescence assay. This can be used as a direct measure of active, comprehensive cell protection, and thus as a measure for a prophylactic effect, if multiple parts are determined (in compartment-specific manner).
Material and Methods For the studies concerning the complementary antioxidant effect of a combination, according to the invention, of *ginseng, ginkgo*, with or without *Crataegus*, the chemiluminescence of the whole blood after stimulation with opsonized zymosan was used. With this method, undesirable influences on cell function, such as those that can occur when working with isolated granulocytes, are avoided, so that a well standardized measurement system is available. Luminol was used as an amplifier; the measurements took place on a Bioluminat LB953.

For the measurement, 0.1 ml whole blood was mixed with 0.4 ml phosphate-buffered saline, which contained 0.1% albumin and 0.1% D-glucose. 0.2 ml double-concentrated opsonized zymosan was used as a starter. With each batch, 50 measurements were carried out over a test time period of 20 minutes. Each individual measurement lasted 1.5 seconds. The measurement temperature was 37° C.

For the various test series, control measurements were carried out, and the various test substances were used.

For this purpose, 500 mg of the extract powder or mixture, in each instance (*ginkgo biloba* extract—extract according to Example 1, *ginkgo* extract powder+*ginseng* root extract according to Example 1, but *ginkgo* diluted 1:10, in each instance, ratio of *ginseng/ginkgo* as in Example 1) were stirred in 50 ml phosphate-buffered saline at 37° C. for 20 minutes. 0.05 ml of the extract obtained was added to the whole blood batch and incubated for 10 minutes until the start of the measurement. The "counts per minute" were recorded during the measurement time period, in each instance, and plotted as a function of time. In FIG. 1, the result is plotted as Cumulative Chemiluminescence AUC (area under the curve), whereby the control measurement is shown on the left. From this, reinforced inhibition and thus an increased antioxidant effect become evident for the *ginkgo+ginseng* combination.

Surprisingly, it is shown that not only is the individual effect of *ginkgo*, for example, maintained, but furthermore it occurs in reinforced manner, and therefore cell protection in different compartments comes about, in additive/synergistic manner, since the individual antioxidant effects are different and act together in the combination according to the invention, in the amount ratio as described, in reinforced manner (tandem effect). This can be explained as follows, without being bound by a specific mechanism: Neuronal, particularly antioxidant/neuronal protection against lipid oxidation is achieved by *ginkgo* extract, with resulting improved circulation. This protection can receive an additional neuroprotective effect reinforcement, achieved as a result of the addition of *ginseng* extract, which lies more within the framework of a lipid peroxidation protective effect, and vice versa, in turn, this brings about a synergistically improved energy availability (compartment-specific tandem effect).

Surprisingly, in addition, particularly due to the stimulation of the formation of superoxide dismutase (SOD) caused by *ginseng*, important metabolites of oxygen can be captured catalytically, i.e. at high reaction kinetics, and this leads to a further compartment-specific synergistic protective effect in the sense of the tandem effect described.

As a whole, this includes a prophylactic effect with regard to age-related mental performance reductions and/or problems.

The invention claimed is:

1. A formulation in the form of a dragee, tablet, or gelatin capsule, for treating or inhibiting a reduction in a subject's mental performance, said formulation comprising a combination of *ginkgo biloba* extract and *ginseng* extract,
    wherein the *ginkgo biloba* extract is an acetone/water extract in a ratio of acetone to water of 60:40 (m/m), and the *ginseng* extract is an ethanol/water extract in a ratio of ethanol to water of 60:40 (v/v),
    and wherein the weight ratio of the *ginkgo biloba* extract to the *ginseng* extract is 1.4:1 to 0.9:1, respectively.

2. The formulation according to claim 1, wherein the weight ratio of the *ginkgo biloba* extract to the *ginseng* extract is 1.3:1 to 1.1:1.

3. The formulation according to claim 1, further comprising a *Crataegus* (hawthorn) powder, selected from the group consisting of dry powder of hawthorn fruits (berries), hawthorn leaves, flowers, and mixtures thereof.

4. The formulation according to claim 3, said formulation comprising 10 to 30% of the *ginkgo biloba* extract, 10 to 28% of the *ginseng* extract, and 1.5 to 6% of the *Crataegus* (hawthorn) powder.

5. The formulation according to claim 1, further comprising one or more phospholipids.

6. A method for treating or inhibiting a reduction in mental performance of a subject in need thereof comprising administering to said subject an effective amount of the formulation according to claim 1.

7. The method according to claim 6, wherein the formulation further comprises a *Crataegus* (hawthorn) powder, selected from among powder of hawthorn fruits (berries), hawthorn leaves, flowers, and mixtures thereof.

8. The method according to claim 6, wherein the formulation further comprises one or more phospholipids.

9. The method according to claim 6 wherein the reduction in mental performance is selected from the group consisting of brain performance problems, fatigue, irritability, depressed mood, anxiety and dizziness, and arterial or peripheral circulation problems.

* * * * *